(12) United States Patent
Harris et al.

(10) Patent No.: US 6,420,557 B1
(45) Date of Patent: Jul. 16, 2002

(54) CRYSTALLINE THERAPEUTIC AGENT

(75) Inventors: Laurence James Harris; Richard Anthony Storey; Albert Shaw Wood, all of Kent (GB)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 09/915,705

(22) Filed: Jul. 26, 2001

Related U.S. Application Data (60) Provisional application No. 60/231,122, filed on Sep. 8, 2000, and provisional application No. 60/290,728, filed on May 14, 2001.

(30) Foreign Application Priority Data

Jul. 28, 2000 (GB) .............................................. 0018656
Mar. 15, 2001 (GB) .............................................. 0106464

(51) Int. Cl.$^7$ ............................................ C07D 487/04
(52) U.S. Cl. ...................................................... 544/262
(58) Field of Search ......................................... 544/262

(56) References Cited

FOREIGN PATENT DOCUMENTS

| WO | WO 9111172 | 8/1991 | ............ A61K/9/00 |
|----|------------|--------|----------------------|
| WO | WO 9402518 | 2/1994 | ............ C08B/37/16 |
| WO | WO 9855148 | 12/1998 | ............ A61K/47/48 |
| WO | WO 99/54333 A1 | * 10/1999 | |
| WO | WO 0127113 | 4/2001 | ............ C07D/487/04 |

* cited by examiner

Primary Examiner—Bruck Kifle
Assistant Examiner—Rao Uppu
(74) Attorney, Agent, or Firm—Peter C. Richardson; Gregg C. Benson; James T. Jones (57) ABSTRACT

A polymorph of 1-{6-ethoxy-5-[3-ethyl-6,7-dihydro-2-(2-methoxyethyl)-7-oxo-2H-pyrazolo[4,3-d]pyrimidin-5-yl]-3-pyridylsulfonyl}-4-ethylpiperazine.

1 Claim, 1 Drawing Sheet

FIG. 1

CRYSTALLINE THERAPEUTIC AGENT

This application is filed claiming priority from co-pending U.S. Provisional application Ser. Nos. 60/231,122 filed Sep. 8, 2000 and 60/290,728 filed May 14, 2001.

The present invention relates to a polymorph of 1-{6-ethoxy-5-[3-ethyl-6,7-dihydro-2-(2-methoxyethyl)-7-oxo-2H-pyrazolo[4,3-d]pyrimidin-5-yl]-3-pyridylsulfonyl}-4-ethylpiperazine having the formula (I):

(I)

having a PXRD pattern substantially as defined hereinafter:

As detailed in WO 01/27113, 1-{6-ethoxy-5-[3-ethyl-6,7-dihydro-2-(2-methoxyethyl)-7-oxo-2H-pyrazolo[4,3-d]pyrimidin-5-yl]-3-pyridylsulfonyl}-4-ethylpiperazine is a potent and selective cGMP $PDE_5$ inhibitor and is especially useful in the treatment of inter alia male erectile dysfunction.

For successful utility within the pharmaceutical industry it is critical that the physicochemical properties of an active material are either known or can be reasonably predicted throughout the necessary processes during both its manufacture and pharmaceutical processing as well as during its shipping, storage and eventual therapeutic use. In some cases compounds can exhibit desirable medicinal properties which cannot be translated directly into a suitable pharmaceutical composition because the active compound itself has unsatisfactory physical properties such as for example poor chemical or processing properties. As such, stable, crystalline materials are highly desirable for use in the pharmaceutical industry as crystalline materials are, in general, more stable than their amorphous counterparts, they have a finite structure which can be reproducibly characterised by X-ray diffraction which can be used to identify the presence of a specific polymorphic form.

The present invention provides the crystal structure of 1-{6-ethoxy-5-[3-ethyl-6,7-dihydro-2-(2-methoxyethyl)-7-oxo-2H-pyrazolo[4,3-d]pyrimidin-5-yl]-3-pyridylsulfonyl}-4-ethylpiperazine.

The crystalline material of 1-{6-ethoxy-5-[3-ethyl-6,7-dihydro-2-(2-methoxyethyl)-7-oxo-2H-pyrazolo[4,3-d]pyrimidin-5-yl]-3-pyridylsulfonyl}-4-ethylpiperazine as defined herein may also be referred to as a non-solvated product of 1-{6-ethoxy-5-[3-ethyl-6,7-dihydro-2-(2-methoxyethyl)-7-oxo-2H-pyrazolo[4,3-d]pyrimidin-5-yl]-3-pyridylsulfonyl}-4-ethylpiperazine wherein a non-solvated product as defined herein means a product which has essentially no retained solvent bound within the crystal lattice or otherwise entrapped or engaged within the crystals. Solvent retained on the surface of the crystal lattice is not included within the definition of retained solvent, although it is preferred that the crystalline material of the present invention does not retain solvent on the surface. Essentially no retained solvent as defined herein means that there is less than 1%, preferably less than about 0.85%, more preferably less than about 0.3% and especially from 0 to 0.25% total retained solvent within the crystal lattice structure or entrapped within the crystals.

The crystals of 1-{6-ethoxy-5-[3-ethyl-6,7-dihydro-2-(2-methoxyethyl)-7-oxo-2H-pyrazolo[4,3-d]pyrimidin-5-yl]-3-pyridylsulfonyl}-4-ethylpiperazine having the XRD pattern as defined hereinafter have a high melting point and early investigations show that they are non-hygroscopic, are stable and have good formulation properties.

The preparation of 1-{6-ethoxy-5-[3-ethyl-6,7-dihydro-2-(2-methoxyethyl)-7-oxo-2H-pyrazolo[4,3-d]pyrimidin-5-yl]-3-pyridylsulfonyl}-4-ethylpiperazine having the formula (I) according to the present invention may be carried out as illustrated in the Example and Preparations sections hereinafter.

The XRD pattern of 1-{6-ethoxy-5-[3-ethyl-6,7-dihydro-2-(2-methoxyethyl)-7-oxo-2H-pyrazolo[4,3-d]pyrimidin-5-yl]-3-pyridylsulfonyl}-4-ethylpiperazine having the formula (I) can be characterised according to the method detailed hereinafter.

X-Ray Diffraction

The single crystal X-ray diffraction (XRD) pattern for 1-{6-ethoxy-5-[3-ethyl-6,7-dihydro-2-(2-methoxyethyl)-7-oxo-2H-pyrazolo[4,3-d]pyrimidin-5-yl]-3-pyridylsulfonyl}-4-ethylpiperazine having Mpt 162–165° C. (as prepared according to the process of Example 1) was determined by single crystal X-ray diffraction. A representative crystal was surveyed and a 1 Å data set (maximum sin $\Theta/\lambda=0.5$) was collected on a Siemens R4RA/v diffractometer. Atomic scattering factors were taken from the International Tables for X-Ray Crystallography (International Tables for X-Ray Crystallography, Vol. IV, pp. 55, 99, 149 Birmingham: Kynoch Press, 1974). All crystallographic calculations were facilitated by the SHELXTL system (G. M. Sheldrick, SHELXTL, User Manual, Nicolet Instruments Co., 1981). All diffractometer data were collected at room temperature.

The simulated powder X-ray diffraction (PXRD) pattern, (as reported in Table 1 for intensities above 1%) was generated from single crystal data using Cerius$^2$ Diffraction-Crystal Module using Radiation=1.54178 Å with a 0.5 Polarisation factor and no monochromator. The crystal size was taken to be 500×500×500 Å$^3$ with Lorentzian peak shape. Diffraction peaks were simulated over the two-theta angle range of 2–55°.

The crystallographic calculations (intensity calculations) were facilitated by use of the SHELXTL system (G. M. Sheldrick, SHELXTL, User Manual, Nicolet Instrument Co., 1981). The final R-index was 4.60%.

The main peaks (in degrees θ) of the simulated PXRD pattern are illustrated in Table 1. Main peaks as defined herein are all those having an intensity above 1%.

TABLE 1

| d-spacing (Å) | Intensity (%) | d-spacing (Å) | Intensity (%) | d-spacing (Å) | Intensity (%) | d-spacing (Å) | Intensity (%) |
|---|---|---|---|---|---|---|---|
| 12.2486 | 1.24 | 4.2323 | 19.04 | 3.061 | 9.18 | 2.4041 | 2.24 |
| 9.7301 | 100 | 4.1595 | 1.19 | 3.0483 | 2.22 | 2.3424 | 1.22 |
| 8.5596 | 36.31 | 4.0421 | 1.35 | 3.0428 | 1.94 | 2.299 | 1.13 |
| 7.3923 | 15.02 | 3.9186 | 7.81 | 2.9929 | 1.59 | 2.264 | 1.23 |
| 7.3856 | 8.35 | 3.8951 | 10.26 | 2.9804 | 2.1 | 2.2605 | 1.29 |
| 7.3284 | 1.69 | 3.8491 | 5.34 | 2.9403 | 3.46 | 2.2079 | 2.65 |
| 5.8222 | 14.49 | 3.8485 | 2.46 | 2.9073 | 1.74 | 2.1855 | 1.9 |
| 5.7617 | 1.96 | 3.8427 | 43.14 | 2.8719 | 1.68 | 2.1679 | 1.92 |
| 5.7461 | 43.25 | 3.7357 | 3.1 | 2.8532 | 4.7 | 2.1468 | 1.35 |
| 5.1166 | 7.17 | 3.6961 | 3.99 | 2.8122 | 11.19 | 2.1119 | 4.52 |
| 5.1078 | 32.71 | 3.6805 | 4.51 | 2.8097 | 2.82 | 2.0769 | 1.15 |
| 4.8807 | 17.47 | 3.6042 | 5.28 | 2.7776 | 2.17 | 2.0471 | 1.12 |
| 4.8674 | 10.85 | 3.5988 | 6.09 | 2.7774 | 1.46 | 2.028 | 1.63 |
| 4.865 | 10.98 | 3.5819 | 6.8 | 2.7162 | 1.76 | 1.9935 | 1.03 |
| 4.8425 | 13.19 | 3.5721 | 8.55 | 2.7041 | 3.63 | 1.9883 | 2.96 |
| 4.8018 | 3.32 | 3.5355 | 2.47 | 2.6875 | 1.42 | 1.9181 | 1.27 |
| 4.7632 | 10.57 | 3.407 | 1.2 | 2.6443 | 2.19 | 1.9058 | 1.03 |
| 4.7491 | 4.16 | 3.3461 | 4.91 | 2.6084 | 3.75 | 1.884 | 1.23 |
| 4.641 | 1.96 | 3.3318 | 7.54 | 2.6025 | 1.6 | 1.8797 | 2.49 |
| 4.629 | 19.73 | 3.3154 | 4.36 | 2.5809 | 1.31 | 1.8749 | 2.81 |
| 4.3314 | 9.53 | 3.2827 | 1.7 | 2.5448 | 1.21 | 1.7939 | 1.57 |
| 4.3301 | 3.65 | 3.2774 | 1.22 | 2.5438 | 3.26 | 1.7617 | 1.24 |
| 4.3066 | 26.66 | 3.2434 | 19.95 | 2.4325 | 2.47 | 1.7379 | 1.82 |
| 4.2909 | 51.91 | 3.224 | 2.11 | 2.4212 | 1.24 | 1.7194 | 1.03 |
| 4.2798 | 24.75 | 3.0663 | 1.38 | 2.4163 | 4.39 | | |

Thus the present invention provides 1-{6-ethoxy-5-[3-ethyl-6,7-dihydro-2-(2-methoxyethyl)-7-oxo-2H-pyrazolo [4,3-d]pyrimidin-5-yl]-3-pyridylsulfonyl}-4-ethylpiperazine material having a PXRD pattern substantially as defined in Table 1 when measured according to the method described hereinbefore.

As will be appreciated by the skilled crystallographer, whilst the relative intensities of the various peaks within Table 1 may vary due to a number of factors such as for example orientation effects of crystals in the X-ray beam or the purity of the material being analysed or the degree of crystallinity of the sample, the peak positions will remain substantially as defined in Table 1.

The skilled crystallographer will also appreciate that measurements using a different wavelength will result in different shifts according to the Bragg equation—$n\lambda=2d \sin \lambda$.

Such further PXRD patterns of 1-{6-ethoxy-5-[3-ethyl-6,7-dihydro-2-(2-methoxyethyl)-7-oxo-2H-pyrazolo[4,3-d]pyrimidin-5-yl]-3-pyridylsulfonyl}-4-ethylpiperazine generated by use of alternative wavelengths are considered to be alternative representations of the PXRD pattern of the crystalline material of the present invention and as such are within the scope of the present invention.

The same compound, as defined by the XRD pattern described in Table 1, when made via alternative routes (as detailed in the Examples section hereinafter) can have a melting point in the range of from 155–165° C. (measured using a Perkin Elmer DSC7/TGA7 at a heating rate of 20° C./minute).

Experiments indicate that the crystalline compound as defined herein tends to exist in one polymorphic form as detailed hereinbefore and as exemplified hereinafter. Monomorphic compounds are particularly desirable for pharmaceutical purposes.

The crystalline compound of the present invention, hereinafter referred to as "the compound" can be administered alone but, in human therapy will generally be administered in admixture with a suitable pharmaceutical excipient diluent or carrier selected with regard to the intended route of administration and standard pharmaceutical practice.

For example, the compound can be administered orally, buccally or sublingually in the form of tablets, capsules (including soft gel capsules), ovules, elixirs, solutions or suspensions, which may contain flavouring or colouring agents, for immediate-, delayed-, modified-, or controlled-release such as sustained-, dual-, or pulsatile delivery applications. The compound may also be administered via intracavernosal injection. The compound may also be administered via fast dispersing or fast dissolving dosages forms or in the form of a high energy dispersion or as coated particles. Suitable pharmaceutical formulations of the compound may be in coated or un-coated form as desired.

Such tablets may contain excipients such as microcrystalline cellulose, lactose, sodium citrate, calcium carbonate, dibasic calcium phosphate, glycine and starch (preferably corn, potato or tapioca starch), disintegrants such as sodium starch glycollate, croscarmellose sodium and certain complex silicates, and granulation binders such as polyvinylpyrrolidone, hydroxypropylmethyl cellulose (HPMC), hydroxypropylcellulose (HPC), sucrose, gelatin and acacia. Additionally, lubricating agents such as magnesium stearate, stearic acid, glyceryl behenate and talc may be included.

Solid compositions of a similar type may also be employed as fillers in gelatin capsules. Preferred excipients in this regard include lactose, starch, a cellulose, milk sugar or high molecular weight polyethylene glycols. For aqueous suspensions and/or elixirs, the compound may be combined with various sweetening or flavouring agents, colouring matter or dyes, with emulsifying and/or suspending agents and with diluents such as water, ethanol, propylene glycol and glycerin, and combinations thereof.

Modified release and pulsatile release dosage forms may contain excipients such as those detailed for immediate release dosage forms together with additional excipients that act as release rate modifiers, these being coated on and/or included in the body of the device. Release rate modifiers include, but are not exclusively limited to, hydroxypropylmethyl cellulose, methyl cellulose, sodium carboxymethylcellulose, ethyl cellulose, cellulose acetate, polyethylene oxide, Xanthan gum, Carbomer, ammonio methacrylate copolymer, hydrogenated castor oil, carnauba wax, paraffin wax, cellulose acetate phthalate, hydroxypropylmethyl cellulose phthalate, methacrylic acid copolymer and mixtures thereof. Modified release and pulsatile release dosage forms may contain one or a combination of release rate modifying excipients. Release rate modifying excipients maybe present both within the dosage form i.e. within the matrix, and/or on the dosage form i.e., upon the surface or coating.

Fast dispersing or dissolving dosage formulations (FDDFs) may contain the following ingredients: aspartame, acesulfame potassium, citric acid, croscarmellose sodium, crospovidone, diascorbic acid, ethyl acrylate, ethyl cellulose, gelatin, hydroxypropylmethyl cellulose, magnesium stearate, mannitol, methyl methacrylate, mint flavouring, polyethylene glycol, fumed silica, silicon dioxide, sodium starch glycolate, sodium stearyl fumarate, sorbitol, xylitol. The terms dispersing or dissolving as used herein to describe FDDFs are dependent upon the solubility of the drug substance used i.e. where the drug substance is insoluble a fast dispersing dosage form can be prepared and where the drug substance is soluble a fast dissolving dosage form can be prepared.

The compound can also be administered parenterally, for example, intracavernosally, intravenously, intra-arterially, intraperitoneally, intrathecally, intraventricularly, intraurethrally intrasternally, intracranially, intramuscularly or subcutaneously, or they may be administered by infusion or needleless injection techniques. For such parenteral administration they are best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well-known to those skilled in the art.

For oral and parenteral administration to human patients, the daily dosage level of the compound will usually be from 10 to 500 mg (in single or divided doses).

Thus, for example, tablets or capsules of the compound may contain from 5 mg to 250 mg of active compound for administration singly or two or more at a time, as appropriate. The physician in any event will determine the actual dosage which will be most suitable for any individual patient and it will vary with the age, weight and response of the particular patient. The above dosages are exemplary of the average case. There can, of course, be individual instances where higher or lower dosage ranges are merited and such are within the scope of this invention. The skilled person will also appreciate that, in the treatment of certain conditions (including MED and FSD), the compound may be taken as a single dose on an "as required" basis (i.e. as needed or desired).

Example Tablet Formulation

In general a tablet formulation could typically contain between about 0.01 mg and 500 mg of the compound whilst tablet fill weights may range from 50 mg to 1000 mg. An example formulation for a 10 mg tablet is illustrated:

| Ingredient | % w/w |
| --- | --- |
| Free acid, Free base or Salt of Compound | 10.000* |
| Lactose | 64.125 |
| Starch | 21.375 |
| Croscarmellose Sodium | 3.000 |
| Magnesium Stearate | 1.500 |

*This quantity is typically adjusted in accordance with drug activity.

The tablets are manufactured by a standard process, for example, direct compression or a wet or dry granulation process. The tablet cores may be coated with appropriate overcoats.

The compound can also be administered intranasally or by inhalation and are conveniently delivered in the form of a dry powder inhaler or an aerosol spray presentation from a pressurised container, pump, spray or nebuliser with the use of a suitable propellant, e.g. dichlorodifluoromethane, trichlorofluoromethane, dichlorotetrafluoroethane, a hydrofluoroalkane such as 1,1,1,2-tetrafluoroethane (HFA 134A [trade mark] or 1,1,1,2,3,3,3-heptafluoropropane (HFA 227EA [trade mark]), carbon dioxide or other suitable gas. In the case of a pressurised aerosol, the dosage unit may be determined by providing a valve to deliver a metered amount. The pressurised container, pump, spray or nebuliser may contain a solution or suspension of the active compound, e.g. using a mixture of ethanol and the propellant as the solvent, which may additionally contain a lubricant, e.g. sorbitan trioleate. Capsules and cartridges (made, for example, from gelatin) for use in an inhaler or insufflator may be formulated to contain a powder mix of a compound of the invention and a suitable powder base such as lactose or starch.

Aerosol or dry powder formulations are preferably arranged so that each metered dose or "puff" contains from 1 to 50 mg of a compound of the invention for delivery to the patient. The overall daily dose with an aerosol will be in the range of from 1 to 50 mg which may be administered in a single dose or, more usually, in divided doses throughout the day.

The compound may also be formulated for delivery via an atomiser. Formulations for atomiser devices may contain the following ingredients as solubilisers, emulsifiers or suspending agents: water, ethanol, glycerol, propylene glycol, low molecular weight polyethylene glycols, sodium chloride, fluorocarbons, polyethylene glycol ethers, sorbitan trioleate, oleic acid.

Alternatively, the compound can be administered in the form of a suppository or pessary, or they may be applied topically in the form of a gel, hydrogel, lotion, solution, cream, ointment or dusting powder. The compound may also be dermally administered. The compound may also be transdermally administered, for example, by the use of a skin patch. The compound may also be administered by the ocular, pulmonary or rectal routes.

For ophthalmic use, the compound can be formulated as micronised suspensions in isotonic, pH adjusted, sterile saline, or, preferably, as solutions in isotonic, pH adjusted, sterile saline, optionally in combination with a preservative such as a benzylalkonium chloride. Alternatively, the compound may be formulated in an ointment such as petrolatum.

For application topically to the skin, the compound of the invention can be formulated as a suitable ointment containing the active compound suspended or dissolved in, for example, a mixture with one or more of the following: mineral oil, liquid petrolatum, white petrolatum, propylene glycol, polyoxyethylene polyoxypropylene compound, emulsifying wax and water. Alternatively, it can be formulated as a suitable lotion or cream, suspended or dissolved in, for example, a mixture of one or more of the following: mineral oil, sorbitan monostearate, a polyethylene glycol, liquid paraffin, polysorbate 60, cetyl esters wax, cetearyl alcohol, 2-octyidodecanol, benzyl alcohol and water.

The compound may also be used in combination with a cyclodextrin. Cyclodextrins are known to form inclusion and non-inclusion complexes with drug molecules. Formation of a drug-cyclodextrin complex may modify the solubility, dissolution rate, bioavailability and/or stability property of a drug molecule. Drug-cyclodextrin complexes are generally useful for most dosage forms and administration routes. As an alternative to direct complexation with the drug the cyclodextrin may be used as an auxiliary additive, e.g. as a carrier, diluent or solubiliser. Alpha-, beta- and gamma-cyclodextrins are most commonly used and suitable examples are described in WO-A-91/11172, WO-A-94/02518 and WO-A-98/55148.

Generally, in humans, oral administration the compound is the preferred route, being the most convenient and, for example in MED, avoiding the well-known disadvantages associated with intracavernosal (i.c.) administration. A preferred oral dosing regimen in MED for a typical man is from 25 to 250 mg of compound when required. In circumstances where the recipient suffers from a swallowing disorder or from impairment of drug absorption after oral administration, the drug may be administered parenterally, sublingually or buccally.

For veterinary use, the compound, or a veterinarily acceptable salt thereof, or a veterinarily acceptable solvate or pro-drug thereof, is administered as a suitably acceptable formulation in accordance with normal veterinary practice and the veterinary surgeon will determine the dosing regimen and route of administration which will be most appropriate for a particular animal.

Thus the invention provides a pharmaceutical composition comprising the crystalline compound of the present invention together with a pharmaceutically acceptable diluent or carrier.

It further provides a veterinary formulation comprising the crystalline compound of the present invention together with a veterinarily acceptable diluent or carrier.

The crystalline material as defined herein may be prepared according to the preparations and Examples hereinafter.

Preparation of Starting Materials for Example 1

Preparation 1

N-[3-Carbamoyl-5-ethyl-1-(2-methoxyethyl)-1H-pyrazol-4-yl}-2-ethoxy-5-(4ethyl-1-piperazinyl sulfonyl)nicotinamide.

(a) 2-Hydroxy-5-sulfonicotinic acid

2-Hydroxynicotinic acid (27 Kg, 194.2 mol) was added portionwise to 30% oleum (58.1 Kg) at 50° C. over 1 hr. This caused an exotherm to 82° C. The reaction mixture was heated further to 140° C. After maintaining this temperature for 12 hrs the reactor contents were cooled to 15 C. and filtered. The filter cake was then re-slurried with acetone (33 Kg) at room temperature, filtered and dried to afford the title compound (35.3 Kg, 83%) as a white solid. Decomposition pt 273° C. δ (DMSO$_{d6}$): 7.93 (1H, d), 8.42 (1H, d). m/z (Found: 220 [M+H]$^+$, 100%. $C_6H_6NO_6S$ requires 220.17).

(b) Ethyl 2-hydroxy-5-sulfonicotinoate

2-Hydroxy-5-sulfonicotinic acid (500 g, 2.28 mol) was dissolved in ethanol (2.5 L) with stirring and heated to 80° C. After 30 mins 0.5 L of solvent was distilled off, then replaced with fresh ethanol (0.5 L) and taken back to 80° C. After a further 60 mins 1.0 L of solvent was distilled off, then replaced with fresh ethanol (1.0 L) and taken back to 80° C. After a further 60 mins 1.0 L of solvent was distilled off, the reaction cooled to 22° C. and stirred for 16 hr. The precipitated product was filtered, washed with ethanol (0.5 L) and dried at 50° C. under vacuum to afford the title compound (416 g, 74%) as a white solid. Decomposition pt 237° C. δ (DMSO$_{d6}$): 1.25 (3H, t), 4.19 (2H,q), 7.66 (1H, d), 8.13 (1H, d). m/z (Found: 248 [M+H]$^+$, 100%. $C_8H_{10}NO_6S$ requires 248.22).

(c) Ethyl 2-chloro-5-chlorosulfonicotinoate

Ethyl 2-hydroxy-5-sulfonicotioate (24.7 g, 0.1 mol) was slurried in thionyl chloride (238 g, 2.0 mol) and dimethylformamide (1.0 mL) with stirring. The reaction mixture was then heated to reflux for 2.5 hr. The bulk of the thionyl chloride was removed under vacuum with residual thionyl chloride removed with a toluene azeotrope to afford the crude title compound (30.7 g, 108%) as a yellow oil. d (CDCl$_3$): 1.46 (3H, t), 4.50 (2H, q), 8.72 (1H, d), 9.09 (1H, d). This was taken directly onto the next step.

(d) Ethyl 2-chloro-5-(4-ethyl-1-piperazinylsulfonyl) nicotinoate

Crude ethyl 2-chloro-5-chlorosulfonicotinoate (30.7 g, 0.1 mol assumed) was dissolved in ethyl acetate (150 mL) with stirring then ice cooled. To this was added a solution of N-ethylpiperazine (11.4 g, 0.1 mol) and triethylamine (22.5 g, 0.22 mol) in ethyl acetate (50 mL), carefully over 30 mins,
keeping the internal temperature below 10° C. Once the addition was complete the reaction was allowed to warm to 22° C. and stir for 1 hr. The solid was filtered off and the remaining filtrate was concentrated under vacuum to afford the crude title compound (37.1 g, 103%) as a crude yellow gum. δ (CDCl$_3$): 1.10 (3H, t), 1.42 (3H, m), 2.50 (2H, m), 2.60 (4H, m), 3.19 (4H, m), 4.43 (2H, q), 8.40 (1H, d), 8.80 (1H, d). m/z (Found: 362 [M+H]$^+$, 100%. $C_{14}H_{21}ClN_3O_4S$ requires 362.85).

(e) Ethyl 2-ethoxy-5-(4-ethyl-1-piperazinylsulfonyl) nicotinoate

A solution of Ethyl 2-chloro-5-(4-ethyl-1-piperazinylsulfonyl)nicotinoate (36.1 g, 0.1 mol) in ethanol (180 mL) was cooled to 10° C. with stirring. Sodium ethoxide (10.2 g, 0.15 mol) was added portionwise keeping the temperature below 20° C. The reaction mixture was then stirred at ambient temperature for 18 hours. The precipitate was filtered off and water (180 mL) added to the filtrate. The filtrate was then heated to 40° C. for 1 hour. Ethanol (180 mL) was then distilled off at ambient pressure and the remaining aqueous solution allowed to cool to ambient temperature. The precipitated product was then filtered off, washed with water and dried under vacuo at 50° C. to afford the title compound (12.6 g, 34%) as a light brown solid. M.p. 66–68° C. δ (CDCl$_3$): 1.04 (3H, t), 1.39 (3H, t), 1.45 (3H, t), 2.41 (2H, q), 2.52 (4H, m), 3.08 (4H, m), 4.38 (2H, q), 2.57 (2H, q), 8.38 (1H, d), 8.61 (1H, d). m/z (Found: 372 [M+H]$^+$, 100%. $C_{16}H_{26}N_3O_5S$ requires 372.46).

(f) 2-Ethoxy-5-(4-ethyl-1-piperazinylsulfonyl) nicotinic acid

Ethyl 2-ethoxy-5-(4-ethyl-1-piperazinylsulfonyl) nicotinoate (10.2 g, 0.0275 mol) was dissolved in toluene (50 mL) and a solution of sodium hydroxide (1.1 g, 0.0275 mol) in water (20 mL) added to it. This two phase mixture was then stirred vigorously at ambient temperature overnight. The aqueous phase was separated off and adjusted to pH=5.6 by addition of c. hydrochloric acid. The precipitated product was slurried with ice cooling for 15 minutes, filtered, water washed and dried under vacuo at 50° C. to afford the title compound (4.1 g, 43%) as an off-white solid. Mpt 206–207° C. δ (CDCl$_3$): 1.25 (3H, t), 1.39 (3H, t), 2.82 (2H, q), 3.03 (4H, m), 3.25 (4H, m), 4.50 (2H, q), 8.25 (1H, d), 8.56 (1H, d). m/z (Found: 344 [M+H]$^+$, 100%. $C_{14}H_{22}N_3O_5S$ requires 344.38).

(g) Ethyl 3-ethyl-1H-pyrazole-5-carboxylate

To a stirred solution of 2,2-dimethoxybutane (10 g, 84.7 mMol) in CH$_2$Cl$_2$ (50 mL) under a nitrogen atmosphere at 0° C. was added pyridine (13.7 mL, 169.5 mMol). The reaction mixture was maintained at 0° C. and a solution of trichloroacetyl chloride (18.9 mL, 169.5 mMol) in CH$_2$CL$_2$ (35 mL) was added over 1 hour with constant stirring. The yellow-orange solution begins to precipitate a white solid as the reaction progresses. The reaction mixture is allowed to warm to room temperature over 20 h. The reaction mixture was diluted with ethanol (150 mL) and re-cooled to 0° C. before treatment with hydrazine hydrate (8.2 mL, 169.5 mMol) as a solution in ethanol (35 mL) over 30 min. The reaction was heated to 50° C. and solvent was distilled at atmospheric pressure. The temperature was increased until the head temperature reached 78° C. Reflux was maintained for a further 2 h, before cooling to room temperature. The reaction mixture was diluted with water (250 mL) and ethanol was removed by evaporation at reduced pressure. The resultant mixture was extracted with $CH_2Cl_2$ (3×200 mL). The combined organics were dried ($MgSO_4$), filtered and evaporated at reduced pressure to afford the title compound as a brown oil, 12.05 g, 85%.

$^1$H NMR (300 MHz, $CDCl_3$): δ=1.20 (3H, t), 1.28 (3H, t), 2.67 (2H, q), 4.29 (2H, q), 6.55 (1H, s), 12.56 (1H, s).

LRMS m/z=167.1 [M−H]$^+$, $C_8H_{12}N_2O_2$ requires 168.2.

(h) Ethyl 3-ethyl-1H-pyrazole-5-carboxylic acid

Aqueous sodium hydroxide solution (10M; 100 ml, 1.0 mol) was added dropwise to a stirred suspension of the title compound of Preparation 1(g) (66.0 g, 0.39 mol) in methanol and the resulting solution heated under reflux for 4 hours. The cool reaction mixture was concentrated under reduced pressure to ca. 200 ml, diluted with water (200 ml) and this mixture washed with toluene (3×100 ml). The resulting aqueous phase was acidified with concentrated hydrochloric acid to pH 4 and the white precipitate collected and dried by suction to provide the title compound (34.1 g).

δ ($DMSO_{d6}$): 1.13 (3H,t), 2.56 (2H,q), 6.42 (1H,s).

(i) 4-Nitro-3-n-propyl-1H-pyrazole-5-carboxylic acid

Fuming sulphuric acid (17.8 ml) was added dropwise to stirred, ice-cooled fuming nitric acid (16.0 ml), the resulting solution heated to 50° C., then 3-n-propyl-1H-pyrazole-5-carboxylic acid (Chem. Pharm. Bull., 1984, 32, 1568; 16.4 g, 0.106 mol) added portionwise over 30 minutes whilst maintaining the reaction temperature below 60° C. The resulting solution was heated for 18 hours at 60° C., allowed to cool, then poured onto ice. The white precipitate was collected, washed with water and dried by suction to yield the title compound (15.4 g), m.p. 170–172° C. Found: C, 42.35; H, 4.56; N, 21.07. $C_7H_9N_3O_4$ requires C, 42.21; H, 4.55; N, 21.10%. δ ($DMSO_{d6}$): 0.90 (3H,t), 1.64 (2H,m), 2.83 (2H,m), 14.00 (1H,s).

(j) 3-Ethyl-4-nitro-1H-pyrazole-5-carboxylic acid

Obtained from the title compound of Preparation 1(h), by analogy with the process of Preparation 1(i), as a brown solid (64%). δ ($DMSO_{d6}$): 1.18 (3H,t), 2.84 (2H,m), 13.72 (1H,s).

(k) 4-Nitro-3-n-propyl-1H-pyrazole-5-carboxamide

A solution of the title compound of Preparation 1(i) (15.4 g, 0.077 mol) in thionyl chloride (75 ml) was heated under reflux for 3 hours and then the cool reaction mixture evaporated under reduced pressure. The residue was azeotroped with tetrahydrofuran (2×50 ml) and subsequently suspended in tetrahydrofuran (50 ml), then the stirred suspension ice-cooled and treated with gaseous ammonia for 1 hour. Water (50 ml) was added and the resulting mixture evaporated under reduced pressure to give a solid which, after trituration with water and drying by suction, furnished the title compound (14.3 g), m.p. 197–199° C. Found: C, 42.35; H, 5.07; N, 28.38. $C_7H_{10}N_4O_3$ requires C, 42.42; H, 5.09; N, 28.27%. δ ($DMSO_{d6}$): 0.90 (3H,t), 1.68 (2H,m), 2.86 (2H,t), 7.68 (1H,s), 8.00 (1H,s).

(l) 3-Ethyl-4-nitro-1H-pyrazole-5-carboxamide

Obtained from the title compound of Preparation 1(j), by analogy with Preparation 1(k), as a white solid (90%). δ ($DMSO_{d6}$): 1.17 (3H,t), 2.87 (2H,m), 7.40 (1H,s), 7.60 (1H,s), 7.90 (1H,s). LRMS: m/z 185 (M+1)$^+$.

(m)(i) 5-Ethyl-1-(2-methoxyethyl)-4-nitro-1H-pyrazole-3-carboxamide.

A mixture of 3-ethyl-4-nitro-1H-pyrazole-5-carboxamide (2.5 kg, 13.6 Mol), sodium carbonate (1.8 Kg, 17.0 Mol) and 2-bromoethyl methyl ether (1.98 kg, 14.2 Mol) in THF (22.5 L) and water (2.5 L) was heated under reflux and stirred for 20 hours. The mixture was cooled to ambient temperature and $CH_2Cl_2$ (67.5 L) and water (22.5 L) were added. The resultant organic and aqueous layers were separated. The aqueous phase was extracted with $CH_2Cl_2$ (22.5 L) and the combined organic solution was distilled under atmospheric pressure and replaced with ethyl acetate (33 L) to a final volume of 17 L. The cooled mixture was granulated at ambient temperature for 2 hours, filtered and washed with ethyl acetate (2.5 L). This afforded 5-ethyl-1-(2-methoxyethyl)-4-nitro-1H-pyrazole-3-carboxamide as a white crystalline solid, 2.10 kg, 57%. m.p.=140° C. Found: C, 44.46; H, 5.79; N, 23.01. $C_9H_{14}N_4O_4$ requires C, 44.63; H, 5.79; N, 23.14%.

δ ($CDCl_3$): 1.18 (3H, t), 2.98 (2H, q), 3.22 (3H, s), 3.77 (2H, t), 4.28 (2H, q), 6.03 (1H, s), 7.36 (1H, s).

LRMS: m/z =243 (M+1)$^+$ (m)(ii) 5-Ethyl-1-(2-methoxyethyl)-4-nitro-1H-pyrazole-3-carboxamide.

A mixture of 3-ethyl-4-nitro-1H-pyrazole-5-carboxamide (25 g, 0.136 Mol), sodium carbonate (18 g, 0.17 Mol) and sodium iodide (20.4 g, 0.136 Mol) were suspended in ethyl methyl ketone (125 mL) at room temperature. 2-bromoethyl methyl ether (12.8 mL, 0.142 Mol) was added and the mixture was heated to reflux and stirred for 70 hours. The mixture was cooled to ambient temperature and water (250 mL) was added. The resultant slurry was warmed to reflux and held at that temperature for 30 min before cooling to room temperature. The resultant precipitate was granulated at room temperature for 3 h, filtered and vacuum dried to afford 5-ethyl-1-(2-methoxyethyl)-4-nitro-1H-pyrazole-3-carboxamide as a yellow crystalline solid 24.3 g, 74%. Data as reported for Preparation 1(m)(i).

(n) 4-Amino-5-ethyl-1-(2-methoxyethyl)-1H-pyrazole-3-carboxamide.

A mixture of 5-ethyl-1-(2-methoxyethyl)-4-nitro-1H-pyrazole-3-carboxamide (20 g, 82.6 mMol) and 5%Pd/C (1 g) in methanol (200 mL) was pressurised at 50 psi/25° C. in a sealed vessel and stirred for 15 hours. At the end of the reaction the mixture was filtered through arbocel and the filter cake was washed with methanol. The methanolic solution was distilled at atmospheric pressure and replaced with ethyl acetate to a final volume of 100 mL. The cooled mixture was granulated at ambient temperature for 2 h filtered and washed with ethyl acetate (20 mL) to afford 4-amino-5-ethyl-1-(2-methoxyethyl)-1H-pyrazole-3-carboxamide as a white crystalline solid, 15 g, 88%. m.p.= 131° C. Found: C, 50.75; H, 7.62; N, 26.38. $C_9H_{16}N_4O_2$ requires C, 50.94; H, 7.55; N, 26.42%.

δ (CDCl$_3$): 1.20 (3H, t), 2.63 (2H, q), 3.32 (3H, s), 3.74 (2H, t), 3.95 (2H, s), 4.15 (2H, t), 5.27 (1H, s), 6.59 (1H, s).
LRMS: m/z=213 (M+1)$^+$

(o) N-[3-Carbamoyl-5-ethyl-1-(2-methoxyethyl)-1H-pyrazol-4-yl}-2-ethoxy-5-(4-ethyl-1-piperazinyl sulfonyl)nicotinamide.

Route (a)

2-ethoxy-5-(4-ethyl-1-piperazinylsulfonyl)nicotinic acid (2.31 kg, 6.73 Mol) was suspended in ethyl acetate (16.2 L) and 1,1-carbonyldimidazole (1.09 kg, 6.73 Mol) was added at room temperature. The reaction mixture was heated at 45° C. for 40 minutes and then the reaction was stirred for a further 40 minutes at reflux. After cooling to ambient temperature 4-amino-5-ethyl-1-(2-methoxyethyl)-1H-pyrazole-3-carboxamide (1.5 kg, 7.06 Mol) was added to the cooled mixture, and the reaction stirred for a further 15 hours under reflux. The mixture was cooled filtered and the filter cake was washed with 90% water/10% ethyl acetate, (2 mL/g) to afford N-[3-carbamoyl-5-ethyl-1-(2-methoxyethyl)-1H-pyrazol-4-yl}-2-ethoxy-5-(4-ethyl-1-piperazinyl sulfonyl)nicotinamide as an off white crystalline solid, 3.16 kg, 88%. m.p.=156° C. Found: C, 51.33; H, 6.56; N, 18.36. $C_{23}H_{35}N_7O_6S$ requires C, 51.40; H, 6.53; N, 18.25%.

δ (CDCl$_3$): 1.04 (3H, t), 1.22 (3H, t), 1.60 (3H, t), 2.44 (2H, q), 2.54 (4H, m), 2.96 (2H, q), 3.12 (4H, m), 3.36 (3H, s), 3.81 (2H, t), 4.27 (2H, t), 4.80(2H, q), 5.35(1H, s), 6.68 (1H, s), 8.66 (1H, d), 8.86 (1H, d), 10.51 (1H, s).
LRMS: m/z=539 (M+1)$^+$

Route (b)

2-ethoxy-5-(4-ethyl-1-piperazinylsulfonyl)nicotinic acid (27.5 g, 0.08 Mol) was suspended in ethyl acetate (0.193 L) and 1,1-carbonyidimidazole (13.3 g, 0.082 Mol) was added at room temperature. The reaction mixture was heated at 45° C. for 15 minutes and then the reaction was stirred for a further 60 minutes at reflux. After cooling to ambient temperature 4-amino-5-ethyl-1-(2-methoxyethyl)-1H-pyrazole-3-carboxamide (16.5 g, 0.078 Mol) was added to the cooled mixture, and the reaction stirred for a further 17 hours under reflux. The solution was cooled and water (0.07 L) and ethyl acetate (0.17 L) added. The slurry was warmed to 40° C. and the organic separated. The organic was concentrated to by evaporating 0.23 L solvent. The slurry was cooled, granulated at 0–-10° C. filtered and the filter cake was washed with 90% water/10% ethyl acetate, (2 mL/g) to afford N-[3-carbamoyl-5-ethyl-1-(2-methoxyethyl)-1H-pyrazol-4-yl}-2-ethoxy-5-(4-ethyl-1-piperazinyl sulfonyl)nicotinamide as an off white crystalline solid, 38.7 g, 89%. m.p.=159–161° C.

δ (CDCl$_3$): 1.04 (3H, t), 1.22 (3H, t), 1.61 (3H, t), 2.42 (2H, q), 2.54 (4H, m), 2.96 (2H, q), 3.12 (4H, m), 3.36 (3H, s), 3.81 (2H, t), 4.27 (2H, t), 4.78(2H, q), 5.35(1H, s), 6.68 (1H, s), 8.66 (1H, d), 8.86 (1H, d), 10.51 (1H, s).
LRMS: m/z=538 (M+1)$^+$

Preparation of Starting Materials for Example 2 a) Pyridine-2-amino-5-sulphonic acid

2-Aminopyridine (80 g, 0.85 mol) was added portionwise over 30 minutes to oleum (320 g) and the resulting solution heated at 140° C. for 4 hours. On cooling, the reaction was poured onto ice (200 g) and the mixture stirred in an ice/salt bath for a further 2 hours. The resulting suspension was filtered, the solid washed with ice water (200 ml) and cold IMS (200 ml) and dried under suction to afford the title compound as a solid, 111.3 g; LRMS: m/z 175 (M+1)$^+$.

b) Pyridine-2-amino-3-bromo-5-sulphonic acid

Bromine (99 g, 0.62 mol) was added dropwise over an hour, to a hot solution of the product from stage a) (108 g, 0.62 mol) in water (600 ml) so as to maintain a steady reflux. Once the addition was complete the reaction was cooled and the resulting mixture filtered. The solid was washed with water and dried under suction to afford the title compound, 53.4 g; δ (DMSO$_{d6}$, 300 MHz): 8.08 (1H, s), 8.14 (1H, s); LRMS: m/z 253(M)$^+$.

c) Pyridine-3-bromo-2-chloro-5-sulphonyl chloride

A solution of sodium nitrite (7.6 g, 110.0 mmol) in water (30 ml) was added dropwise to an ice-cooled solution of the product from stage b) (25.3 g, 100.0 mmol) in aqueous hydrochloric acid (115 ml, 20%), so as to maintain the temperature below 6° C. The reaction was stirred for 30 minutes at 0° C. and for a further hour at room temperature. The reaction mixture was evaporated under reduced pressure and the residue dried under vacuum at 70° C. for 72 hours. A mixture of this solid, phosphorus pentachloride (30.0 g, 144 mmol) and phosphorus oxychloride (1 ml, 10.8 mmol) was heated at 125° C. for 3 hours, and then cooled. The reaction mixture was poured onto ice (100 g) and the resulting solid filtered, and washed with water. The product was dissolved in dichloromethane, dried (MgSO$_4$), and evaporated under reduced pressure to afford the title compound as a yellow solid, 26.58 g; δ (CDCl$_3$, 300MHz): 8.46 (1H, s), 8.92 (1H, s).

d) 3-Bromo-2-chloro-5-(4-ethylpiperazin-1-ylsulrhonyl)pyridine

A solution of 1-ethylpiperazine (11.3 mi, 89.0 mmol) and triethylamine (12.5 ml, 89.0 mmol) in dichloromethane (150 ml) was added dropwise to an ice-cooled solution of the product from stage c) (23.0 g, 79.0 mmol) in dichloromethane (150 ml) and the reaction stirred at 0° C. for an hour. The reaction mixture was concentrated under reduced pressure and the residual brown oil was purified by column chromatography on silica gel, using an elution gradient of dichloromethane:methanol (99:1 to 97:3) to afford the title compound as an orange solid, 14.5 g; δ (CDCl$_3$, 300 MHz): 1.05 (3H, t), 2.42 (2H, q), 2.55 (4H, m), 3.12 (4H, m), 8.24 (1H, s), 8.67 (1H, s).

e) 3-Bromo-2-ethoxy-5-(4-ethylpiperazin-1-ylsulphonyl)rvridine

A mixture of the product from stage d) (6.60 g, 17.9 mmol) and sodium ethoxide (6.09 g, 89.55 mmol) in ethanol (100 ml) was heated under reflux for 18 hours, then cooled. The reaction mixture was concentrated under reduced pressure, the residue partitioned between water (100 ml) and ethyl acetate (100 ml), and the layers separated. The aqueous phase was extracted with ethyl acetate (2×100 ml), the combined organic solutions dried (MgSO$_4$) and evaporated under reduced pressure to afford the title compound as a brown solid, 6.41 g; Found: C, 41.27; H, 5.33; N, 11.11. $C_{13}H_{20}BrN_3O_3S$ requires C, 41.35; H, 5.28; N, 10.99%; δ (CDCl$_3$, 300 MHz): 1.06 (3H, t), 1.48 (3H, t), 2.42 (2H, q), 2.56 (4H, m), 3.09 (4H, m), 4.54 (2H, q), 8.10 (1H, s), 8.46 (1H, s); LRMS : m/z 378, 380 (M+1)$^+$.

f) Pyridine 2-ethoxy-5-(4-ethylpiperazin-1-ylsulphonyl)-3-carboxylic acid ethyl ester

A mixture of the product from stage e) (6.40 g, 16.92 mmol), triethylamine (12 ml, 86.1 mmol), and palladium (0) tris(triphenylphosphine) in ethanol (60 ml) was heated at 100° C. and 200 psi, under a carbon monoxide atmosphere, for 18 hours, then cooled. The reaction mixture was evaporated under reduced pressure and the residue purified by column chromatography on silica gel, using an elution gradient of dichloromethane:methanol (100:0 to 97:3) to afford the title compound as an orange oil, 6.2 g; δ (CDCl$_3$, 300 MHz): 1.02 (3H, t), 1.39 (3H, t), 1.45 (3H, t), 2.40 (2H, q), 2.54 (4H, m), 3.08 (4H, m), 4.38 (2H, q), 4.55 (2H, q), 8.37 (1H, s), 8.62 (1H, s); LRMS: m/z 372 (M+1)$^+$.

g) Pyridine 2-ethoxy-5-(4-ethylpiperazin-1-ylsulphonyl)-3-carboxylic acid

A mixture of the product from stage f) (4.96 g, 13.35 mmol) and aqueous sodium hydroxide solution (25 ml, 2N, 50.0 mmol) in ethanol (25 ml) was stirred at room temperature for 2 hours. The reaction mixture was concentrated under reduced pressure to half it's volume, washed with ether and acidified to pH 5 using 4N hydrochloric acid. The aqueous solution was extracted with dichloromethane (3×30 ml), the combined organic extracts dried (MgSO$_4$) and evaporated under reduced pressure to afford the title compound as a tan coloured solid, 4.02 g; δ (DMSO$_{d6}$, 300 MHz): 1.18 (3H, t), 1.37 (3H, t), 3.08 (2H, q), 3.17–3.35 (8H, m), 4.52 (2H, q), 8.30 (1H, s), 8.70 (1H, s).

h) 4-[2-Ethoxy-5-(4-ethylpiperazin-1-ylsulphonyl)pyridin-3-ylcarboxamido]-1H-3-ethylpyrazole-5-carboxamide A solution of 4-amino-3-ethyl-1H-pyrazole-5-carboxamide (WO 9849166, preparation 8) (9.2 g, 59.8 mmol) in N,N-dimethylformamide (60 ml) was added to a solution of the product from stage g) (21.7 g, 62.9 mmol), 1-hydroxybenzotriazole hydrate (10.1 g, 66.0 mmol) and triethylamine (13.15 ml, 94.3 mmol) in dichloromethane (240 ml). 1-(3-Dimethylaminopropyl)-3-ethylcarbodiimide hydrochloride (13.26 g, 69.2 mmol) was added and the reaction stirred at room temperature for 6 hours. The dichloromethane was removed under reduced pressure, the remaining solution poured into ethyl acetate (400 ml), and this mixture washed with aqueous sodium bicarbonate solution (400 ml). The resulting crystalline precipitate was filtered, washed with ethyl acetate and dried under vacuum, to afford the title compound, as a white powder, 22 g; δ (CDCl$_3$+1 drop DMSO$_{d6}$) 0.96 (3H, t), 1.18 (3H, t), 1.50 (3H, t), 2.25–2.56 (6H, m), 2.84 (2H, q), 3.00 (4H, m), 4.70 (2H, q), 5.60 (1H, br s), 6.78 (1H, br s), 8.56 (1H, d), 8.76 (1H, d), 10.59 (1H, s), 12.10–12.30 (1H, s); LRMS: m/z 480 (M+1)$^+$.

i) 2-Methoxyethyl-4-[2-ethoxy-5-(4-ethylpiperazin-1-ylsulphonyl)pyridin-3-ylcarboxamido1-3-ethyloyrazole-5-carboxamide

2-ethoxy-5-(4-ethyl-1-piperazinylsulfonyl)nicotinic acid (2.31 kg, 6.73 Mol) was suspended in ethyl acetate (16.2 L) and 1,1-carbonyldimidazole (1.09 kg, 6.73 Mol) was added at room temperature. The reaction mixture was heated at 45° C. for 40 minutes and then the reaction was stirred for a further 40 minutes at reflux. After cooling to ambient temperature 4-amino-5-ethyl-1-(2-methoxyethyl)-1H-pyrazole-3-carboxamide (1.5 kg, 7.06 Mol) was added to the cooled mixture, and the reaction stirred for a further 15 hours under reflux. The mixture was cooled filtered and the filter cake was washed with 90% water/0% ethyl acetate, (2 mL/g) to afford N-[3-carbamoyl-5-ethyl-1-(2-methoxyethyl)-1H-pyrazol-4-yl}-2-ethoxy-5-(4-ethyl-1-piperazinyl sulfonyl)nicotinamide as an off white crystalline solid, 3.16 kg, 88%. m.p.=156° C. Found: C, 51.33; H, 6.56; N, 18.36. C$_{23}$H$_{35}$N$_7$O$_6$S requires C, 51.40; H, 6.53; N, 18.25%.

δ (CDCl$_3$): 1.04 (3H, t), 1.22 (3H, t), 1.60 (3H, t), 2.44 (2H, q), 2.54 (4H, m), 2.96 (2H, q), 3.12 (4H, m), 3.36 (3H, s), 3.81 (2H, t), 4.27 (2H, t), 4.80(2H, q), 5.35(1H, s), 6.68 (1H, s), 8.66 (1H, d), 8.86 (1H, d), 10.51 (1H, s).

LRMS: m/z=539 (M+1)$^+$

Preparation 3

1-(6-Ethoxy-5-[3-ethyl]-6,7-dihydro-2-(2-methoxyethyl)-7-oxo-2H-pyrazole[4,3d]pyrimidin-5-yl]-3-pyridylsulfonyl)-4-ethylpiperazine.ethyl acetate solvate.

Route (a)

To prepare the compound of Preparation 3 a mixture of the title compound of Preparation 1, N-[3-carbamoyl-5-ethyl-1-(2-methoxyethyl)-1H-pyrazol-4-yl}-2-ethoxy-5-(4-ethyl-1-piperazinyl sulfonyl)nicotinamide, (1.18 kg, 2.2 Mol), potassium tert-butoxide (500 g, 4.4 moles) and ethyl acetate (193 g) in ethanol (11.8 L) was heated at 120° C. for 20 hours. The reaction mixture was then concentrated under reduced pressure, in total approx. 10 L of solvent were distilled. To the residue water (2.9 L) was added and the mixture stirred at room temperature while aqueous HCl was added until pH 7.5 was obtained. Ethyl acetate (7.5 L) was added and the two phase mixture was warmed to 55° C. The organic phase was separated and the aqueous phase was extracted with further ethyl acetate (3.0 L). The combined organic phases were distilled at atmospheric pressure to a final volume of 4 L. The precipitated solids were granulated at 5° C. for 1 h, filtered and washed with ethyl acetate (1.2 L) and dried under vacuum. This afforded 1-(6-Ethoxy-5-[3-ethyl]-6,7-dihydro-2-(2-methoxyethyl)-7-oxo-2H-pyrazole[4,3-d]pyrimidin-5-yl]-3-pyridylsulfonyl)-4-ethylpiperazine as a light yellow crystalline solid, 877 g, 78%. m.p.=157° C. Found: C, 52.65; H, 6.46; N, 17.76. $C_{23}H_{33}N_7O_5S$. 0.2 $C_2H_5CO_2CH_3$ requires C, 53.21; H, 6.49; N, 18.25%.

δ (CDCl$_3$): 1.07 (3H, t), 1.42 (3H, t), 1.61 (3H, t), 2.44 (2H, q), 2.57 (4H, m), 3.08 (2H, q), 3.15 (4H, m), 3.32 (3H, s), 3.92 (2H, q), 4.48 (2H, q), 4.77 (2H, q), 8.65 (1H, d), 9.06 (1H, d). The spectrum also has signals that correspond to a solvate with ethyl acetate.

LRMS: m/z=520 (M+1)$^+$

Route (b)

To prepare the compound of Preparation 3 a mixture of the title compound of Preparation 1, N-[3-carbamoyl-5-ethyl-1-(2-methoxyethyl)-1H-pyrazol-4-yl}-2-ethoxy-5-(4-ethyl-1-piperazinyl sulfonyl)nicotinamide, 34.6 g, 0.064 Mol), potassium tert-butoxide (14.8 g, 0.132 moles) and ethyl acetate (8.5 g 0.096 moles) in ethanol (0.26 L) was heated at 105–107° C. for 17 hours. The reaction mixture was then concentrated under reduced pressure, in total approx. 0.16 L of solvent were distilled. To the remaining oil, water (0.28 L) was added and the mixture stirred at room temperature while aqueous HCl was added until pH 7.5 was obtained. The precipitated solids were granulated at –100° C. to 0° C. for 1 h, filtered and washed with ethanol (0.4 L) and dried under vacuum. This afforded 1-(6-Ethoxy-5-[3-ethyl]-6,7-dihydro-2-(2-methoxyethyl)-7-oxo-2H-pyrazole[4,3d]pyrimidin-5-yl]-3-pyridylsulfonyl)-4-ethylpiperazine as a light yellow crystalline solid, 23.3 g, 69.7%. m.p.= 168–170° C.

δ (CDCl$_3$): 1.07 (3H, t), 1.42 (3H, t), 1.61 (3H, t), 2.44 (2H, q), 2.57 (4H, m), 3.08 (2H, q), 3.15 (4H, m), 3.32 (3H, s), 3.92 (2H, q), 4.48 (2H, q), 4.77 (2H, q), 8.64 (1H, d), 9.05 (1H, d).

LRMS: m/z=520 (M+1)$^+$

EXAMPLE 1

1-{6-ethoxy-5-[3-ethyl-6,7-dihydro-2-(2-methoxyethyl)-7-oxo-2H-pyrazolo]4.3d]pyrimidin-5-yl]-3-pyridylsulfonyl}-4-ethylpiperazine 10 g (0.019 mol) of the title compound of Preparation 3(a), 1-{6-ethoxy-5-[3ethyl-6,7-dihydro-2-(2-methoxyethyl)-7-oxo-2H-pyrazolo[4,3-d]pyrimidin-5-yl]-3-pyridylsulfonyl}-4-ethylpiperazine ethyl acetate solvate, was charged followed by 12 mVg (120 mls) of 16% water in ethyl alcohol. The slurry was heated to reflux to yield a solution and 6 mVg (60 mls) distilled off at atmospheric pressure. The solution was then cooled to room temperature with crystallisation occurring at 40° C. The slurry was then cooled to 5–10° C. and granulated for 30 minutes following which it was filtered and washed with 2 ml/g ethyl alcohol (20 mls). The damp solid was dried in vacuo overnight at 55–60° C. to yield a white crystalline solid. (Yield 7.6 g, 76%). Melting Point 162–165° C.

δ (CDCl$_3$): 1.05 (3H,t), 1.42 (3H,t), 1.58 (3H,t), 2.43 (2H,q), 2.57 (4H,t), 3.09 (2H, t), 3.15 (4H,t), 3.30 (3H,s), 3.93 (2H,t), 4.48 (2H,t), 4.90 (2H,q), 8.65 (1H,d), 9.05 (1H,d), 10.65 (1H,s).

EXAMPLE 2

1-{6-ethoxy-5-[3-ethyl-6,7-dihydro-2-(2-methoxyethyl)-7-oxo-2H-pyrazolo[4,3-d]pyrimidin-5-yl]-3-pyridylsulfonyl}-4-ethylpiperazine 10 g (0.019 mol) of the title compound of Preparation 3(b), 1-{6-ethoxy-5-[3-ethyl-6,7-dihydro-2-(2-methoxyethyl)-7-oxo-2H-pyrazolo[4,3-d]pyrimidin-5-yl]-3-pyridylsulfonyl}-4-ethylpiperazine ethyl acetate solvate, was charged followed by 12 ml/g (120 mls) of 16% water in ethyl alcohol. The slurry was heated to reflux to yield a solution and 9.5 ml/g (60 mls) distilled off at atmospheric pressure. The solution was then cooled to room temperature with crystallisation occurring at 40° C. The slurry was then cooled to 0—10° C. and granulated for 30 minutes following which it was filtered and washed with 2 ml/g ethyl alcohol (20 mls). The damp solid was dried in vacuo overnight at 55–60° C. to yield a white crystalline solid. (Yield 9.4 g, 94%). Melting Point 158–160° C.

δ (CDCl$_3$): 1.05 (3H,t), 1.42 (3H,t), 1.58 (3H,t), 2.43 (2H,q), 2.57 (4H,t), 3.09 (2H, t), 3.15 (4H,t), 3.30 (3H,s), 3.93 (2H,t), 4.48 (2H,t), 4.90 (2H,q), 8.65 (1H,d), 9.05 (1H,d), 10.65 (1H,s).

In the processes of the Examples water and pharmaceutically acceptable alcohols such as methanol, ethanol, propanol preferably ethanol or isopropanol and mixtures thereof can be used. These processes can also be used for the recrystallisation of the title compound.

As will be appreciated by the skilled chemist solvates may be prepared by a variety of standard techniques as are known in the art.

Further solvates of 1-{6-ethoxy-5-[3-ethyl-6,7-dihydro-2-(2-methoxyethyl)-7-oxo-2H-pyrazolo[4,3-d]pyrimidin-5-yl]-3-pyridylsulfonyl}-4-ethylpiperazine can be prepared from either the ethyl acetate solvate (the compound of Preparation 3) or from the compounds of Examples 1 or 2. Such further solvates may be prepared for example by:

(a) slurrying the starting compound over an extended period (such as for example about 2 weeks) with the solvent to be tested (e.g. acetonitrile), followed by filtration of solid material and subsequent PXRD analysis (as defined hereinbefore) of said "wet" i.e. non-dried solid material (solvated) material; or (b) dissolution of the starting compound in the solvent to be tested (e.g. acetonitrile) followed by recrystallisation of the desired solvate from said solution by any appropriate means such as for example, cooling or evaporation techniques and subsequent analysis (using standard PXRD techniques or infra red analysis as are known in the art) of said "wet" i.e. non-dried solid (solvated) material.

The crystalline compound as defined hereinbefore can be generated from solvates thereof via de-solvation using techniques as are standard in the art such as for example via heat treatment (at preferably from about 100° C. up to about 150° C.) or using vacuum techniques (from ambient temperature and above) or via slurrying in a non-solvating solvent (e.g. as illustrated in Examples 1 and 2).

The skilled chemist may utilise alternative drying techniques to generate the crystalline compound as defined hereinbefore.

Further solvates of 1-{6-ethoxy-5-[3-ethyl-6,7-dihydro-2-(2-methoxyethyl)-7-oxo-2H-pyrazolo[4,3-d]pyrimidin-5-yl]-3-pyridylsulfonyl}-4-ethylpiperazine which have been prepared include : n-butanol, methylethylketone (MEK), acetonitrile, tetrahydrofuran, toluene. The presence of solvated material can be qualified via PXRD.

For example an acetonitrile solvate of 1-{6-ethoxy-5-[3-ethyl-6,7-dihydro-2-(2-methoxyethyl)-2H-pyrazolo[4,3-d]pyrimidin-5-yl]-3-pyridylsulfonyl}-4-ethylpiperazine was prepared by firstly dissolving the material in hot acetonitrile followed by slow cooling and subsequent granulation at ambient temperature overnight. The solution was then filtered under vacuum and the resultant solid material (the solvate) allowed to dry at ambient temperature and pressure. The presence of the solvate was detected using PXRD. An alternative method for detection of the solvate is by monitoring the weight loss by TGA. The solvate from acetonitrile is present as the hemisolvate although other solvates may be possible.

These solvated materials have been demonstrated to generate the amorphous free base of 1-{6-ethoxy-5-[3-ethyl-6,7-dihydro-2-(2-methoxyethyl)-7-oxo-2H-pyrazolo[4,3-d]pyrimidin-5-yl]-3-pyridylsulfonyl}-4-ethylpiperazine when dried at about 150° C. as illustrated by Differential Scanning Calorimetry DSC).

The DSC experiments herein were performed using a (measured using a Perkin Elmer DSC7/TGA7 at a heating rate of 20° C./minute).

Figure 1:
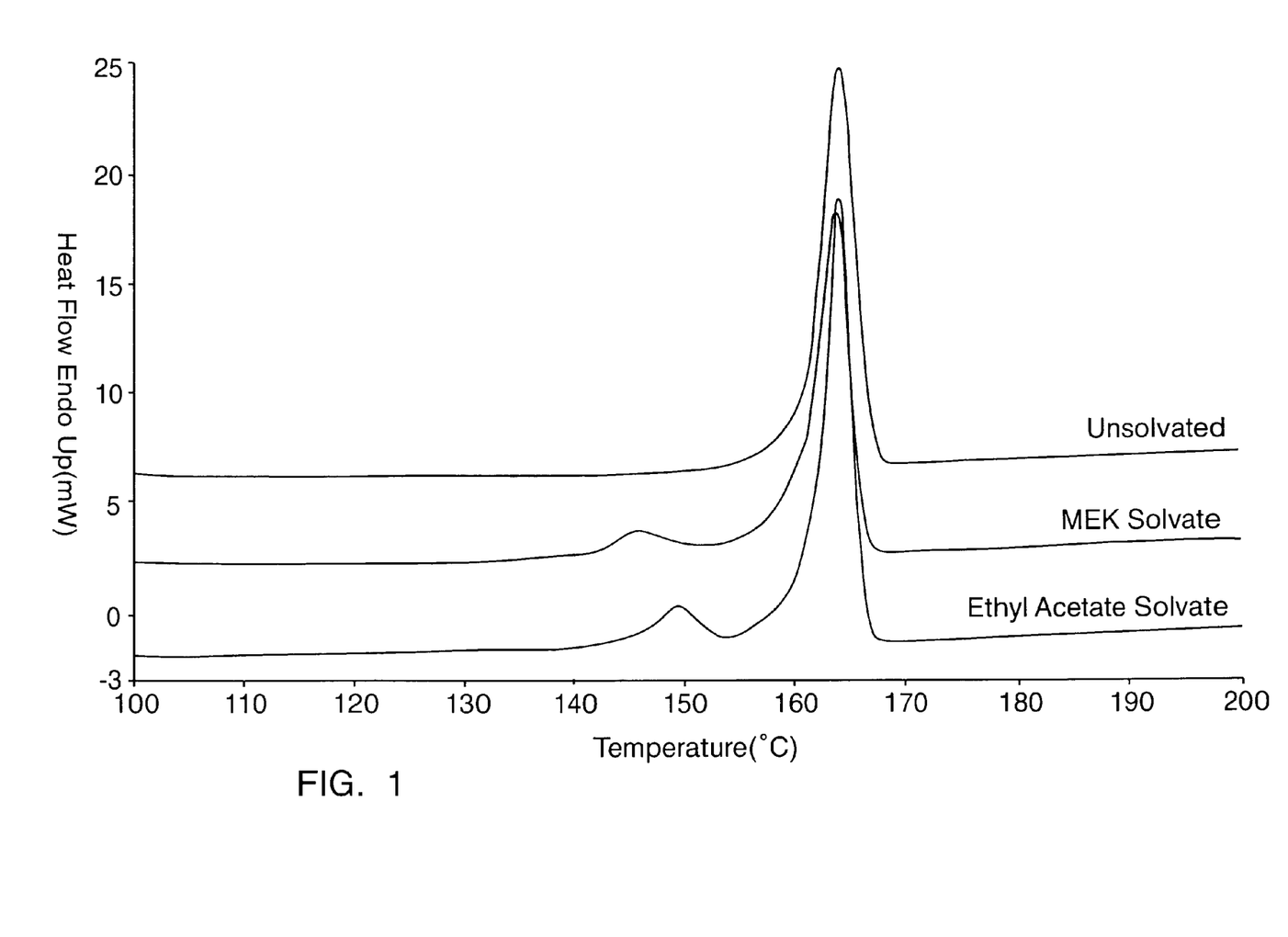
FIG. 1 is a DSC trace which illustrates that both ethyl acetate and methyl ethyl ketone (MEK) solvates are firstly desolvated to release the crystalline material as defined herein which is then melted upon heating at from about 160°–165° C.

FIG. 1 hereinafter illustrates the DSC trace of: the crystalline material having PXRD pattern as illustrated in Table 1 (the compound of Example 1); the DSC trace of the ethyl acetate solvate (the compound of Preparation 3); the DSC trace of the acetonitrile solvate (of the compound of Example 1, wherein said solvate was prepared as detailed hereinbefore).

What is claimed is:

1. A polymorph of 1-{6-ethoxy-5-[3-ethyl-6,7-dihydro-2-(2-methoxyethyl)-7-oxo-2H-pyrazolo[4,3-d]pyrimidin-5-yl]-3-pyridylsulfonyl}-4-ethylpiperazine having a simulated powder X-ray diffraction pattern with main peaks substantially as defined below:

| d-spacing (Å) | Intensity (%) |
| --- | --- |
| 12.2468 | 1.24 |
| 9.7301 | 100 |
| 8.5596 | 36.31 |
| 7.3923 | 15.02 |
| 7.3856 | 8.35 |
| 7.3284 | 1.69 |
| 5.8222 | 14.49 |
| 5.7617 | 1.96 |
| 5.7461 | 43.25 |
| 5.1166 | 7.17 |
| 5.1078 | 32.71 |
| 4.8807 | 17.47 |
| 4.8674 | 10.85 |
| 4.865 | 10.98 |

-continued

| d-spacing (Å) | Intensity (%) |
|---|---|
| 4.8425 | 13.19 |
| 4.8018 | 3.32 |
| 4.7632 | 10.57 |
| 4.7491 | 4.16 |
| 4.641 | 1.96 |
| 4.629 | 19.73 |
| 4.3314 | 9.53 |
| 4.3301 | 3.65 |
| 4.3066 | 26.66 |
| 4.2909 | 51.91 |
| 7.2798 | 24.75 |
| 4.2323 | 19.04 |
| 4.1595 | 1.19 |
| 4.0421 | 1.35 |
| 3.9186 | 7.81 |
| 3.8951 | 10.26 |
| 3.8491 | 5.34 |
| 3.8485 | 2.46 |
| 3.8427 | 43.14 |
| 3.7357 | 3.1 |
| 3.6961 | 3.99 |
| 3.6805 | 4.51 |
| 3.6042 | 5.28 |
| 3.5988 | 6.09 |
| 3.5819 | 6.8 |
| 3.5721 | 8.55 |
| 3.5355 | 2.47 |
| 3.407 | 1.2 |
| 3.3461 | 4.91 |
| 3.3318 | 7.54 |
| 3.3154 | 4.36 |
| 3.2827 | 1.7 |
| 3.2774 | 1.22 |
| 3.2434 | 19.95 |
| 3.224 | 2.11 |
| 3.0663 | 1.38 |
| 3.061 | 9.18 |
| 3.0483 | 2.22 |
| 3.0428 | 1.94 |
| 2.9929 | 1.59 |
| 2.9804 | 2.1 |
| 2.9403 | 3.46 |
| 2.9073 | 1.74 |
| 2.8719 | 1.68 |
| 2.8532 | 4.7 |
| 2.8122 | 11.19 |
| 2.8097 | 2.82 |
| 2.7776 | 2.17 |

-continued

| d-spacing (Å) | Intensity (%) |
|---|---|
| 2.7774 | 1.46 |
| 2.7162 | 1.76 |
| 2.7041 | 3.63 |
| 2.6875 | 1.42 |
| 2.6443 | 2.19 |
| 2.6084 | 3.75 |
| 2.6025 | 1.6 |
| 2.5809 | 1.31 |
| 2.5448 | 1.21 |
| 2.5438 | 3.26 |
| 2.4325 | 2.47 |
| 2.4212 | 1.24 |
| 2.4163 | 4.39 |
| 2.4041 | 2.24 |
| 2.3424 | 1.22 |
| 2.299 | 1.13 |
| 2.264 | 1.23 |
| 2.2605 | 1.29 |
| 2.2079 | 2.65 |
| 2.1855 | 1.9 |
| 2.1679 | 1.92 |
| 2.1468 | 1.35 |
| 2.1119 | 4.52 |
| 2.0769 | 1.15 |
| 2.0471 | 1.12 |
| 2.028 | 1.63 |
| 1.9935 | 1.03 |
| 1.9883 | 2.96 |
| 1.9181 | 1.27 |
| 1.9058 | 1.03 |
| 1.884 | 1.23 |
| 1.8797 | 2.49 |
| 1.8749 | 2.81 |
| 1.7939 | 1.57 |
| 1.7617 | 1.24 |
| 1.7379 | 1.82 |
| 1.7194 | 1.03 | wherein said PXRD pattern is generated using copper K-alpha1 X-rays having a wavelength of 1.54178 Angstroms.

* * * * *